(12) United States Patent
Gentner et al.

(10) Patent No.: US 8,776,790 B2
(45) Date of Patent: Jul. 15, 2014

(54) WIRELESS, GAS FLOW-POWERED SENSOR SYSTEM FOR A BREATHING ASSISTANCE SYSTEM

(75) Inventors: Julien Gentner, Saunay (FR); Pascal Nicolazzi, Gondreville (FR); Laurent Mougel, Sainte Marguerite (FR); Bertrand Poirot, Villers les Nancy (FR); Philippe Perine, Eulmont (FR)

(73) Assignee: Covidien LP, Mansfield, MA (US)

( * ) Notice: Subject to any disclaimer, the term of this patent is extended or adjusted under 35 U.S.C. 154(b) by 783 days.

(21) Appl. No.: 12/504,471

(22) Filed: Jul. 16, 2009

(65) Prior Publication Data

US 2011/0011400 A1 Jan. 20, 2011

(51) Int. Cl.
*A61M 16/00* (2006.01)
*H02K 7/18* (2006.01)

(52) U.S. Cl.
USPC ........................................ 128/204.18; 290/52

(58) Field of Classification Search
USPC ............. 128/200.24, 204.18, 204.21–204.23, 128/204.26, 204.29, 290.52; 136/243; 290/52
See application file for complete search history.

(56) References Cited

U.S. PATENT DOCUMENTS

| | | |
|---|---|---|
| 3,796,951 A | 3/1974 | Joseph |
| 4,497,881 A | 2/1985 | Bertolino |
| 4,559,456 A | 12/1985 | Yamamoto et al. |
| 4,662,736 A | 5/1987 | Taniguchi et al. |
| 4,752,089 A | 6/1988 | Carter |
| 4,921,642 A | 5/1990 | LaTorraca |
| 4,954,799 A | 9/1990 | Kumar |
| 4,965,462 A | 10/1990 | Crawford |
| 4,967,744 A | 11/1990 | Chua ........................ 128/204.18 |
| 5,015,544 A | 5/1991 | Burroughs et al. |
| 5,057,822 A | 10/1991 | Hoffman |
| 5,072,737 A | 12/1991 | Goulding |

(Continued)

FOREIGN PATENT DOCUMENTS

| | | |
|---|---|---|
| EP | 850652 | 7/1998 |
| FR | 2824907 A1 | 11/2002 |

(Continued)

OTHER PUBLICATIONS

PCT Notification of Transmittal of the International Search Report and the Written Opinion of the International Searching Authority, or the Declaration, Date of mailing: Sep. 20, 2010, Applicant's File reference: WO, International Application No. PCT/US2010/035453, International Filing Date: May 29, 2010, Applicant: Nellcor Puritan Bennett LLC.

(Continued)

*Primary Examiner* — Tan-Uyen T Ho
*Assistant Examiner* — Mark Wardas

(57) ABSTRACT

A breathing assistance system for providing breathing assistance to a patient includes a gas delivery system configured to generate a gas flow, a patient interface configured to interface with the patient, a connection system connected between the gas delivery system and the patient interface and configured to communicate the gas flow to the patient interface for delivery to the patient, and a sensor system remote from the gas delivery system and connected to at least one of the patient interface and the connection system. The sensor system may include a sensor for measuring a parameter, one or more actuators, and a power supply based on a turbine configured to be driven by the gas flow and an electrical generator coupled to the turbine and configured to generate electricity.

18 Claims, 4 Drawing Sheets

(56) References Cited

U.S. PATENT DOCUMENTS

| | | | |
|---|---|---|---|
| 5,099,836 A | 3/1992 | Rowland et al. ......... 128/204.23 |
| 5,111,827 A | 5/1992 | Rantala ................... 128/204.21 |
| 5,118,962 A | 6/1992 | Ishii et al. |
| 5,146,092 A | 9/1992 | Apperson et al. |
| 5,149,603 A | 9/1992 | Fleming et al. |
| 5,150,291 A | 9/1992 | Cummings et al. |
| 5,153,436 A | 10/1992 | Apperson et al. |
| 5,156,931 A | 10/1992 | Burroughs et al. |
| 5,159,272 A | 10/1992 | Rao et al. |
| 5,161,525 A | 11/1992 | Kimm et al. |
| 5,216,371 A | 6/1993 | Nagai |
| 5,237,987 A | 8/1993 | Anderson et al. |
| 5,244,754 A | 9/1993 | Bohmer et al. |
| 5,256,500 A | 10/1993 | Ishimoto |
| 5,258,901 A | 11/1993 | Fraidlin |
| 5,271,389 A | 12/1993 | Isaza et al. |
| 5,279,549 A | 1/1994 | Ranford |
| 5,283,137 A | 2/1994 | Ching |
| 5,299,568 A | 4/1994 | Forare et al. |
| 5,301,921 A | 4/1994 | Kumar |
| 5,306,956 A | 4/1994 | Ikeda et al. |
| 5,308,715 A | 5/1994 | Aronne |
| 5,315,228 A | 5/1994 | Hess et al. |
| 5,316,009 A | 5/1994 | Yamada |
| 5,319,540 A | 6/1994 | Isaza et al. |
| 5,325,861 A | 7/1994 | Goulding |
| 5,333,606 A | 8/1994 | Schneider et al. |
| 5,339,807 A | 8/1994 | Carter |
| 5,343,857 A | 9/1994 | Schneider et al. |
| 5,348,813 A | 9/1994 | Bohmer et al. |
| 5,350,640 A | 9/1994 | Masui |
| 5,351,522 A | 10/1994 | Lura |
| 5,357,946 A | 10/1994 | Kee et al. |
| 5,368,019 A | 11/1994 | LaTorraca |
| 5,369,277 A | 11/1994 | Knodle et al. |
| 5,369,802 A | 11/1994 | Murray |
| 5,370,112 A | 12/1994 | Perkins |
| 5,372,898 A | 12/1994 | Atwater et al. |
| 5,383,449 A | 1/1995 | Forare et al. |
| 5,385,142 A | 1/1995 | Brady et al. |
| 5,389,470 A | 2/1995 | Parker et al. |
| 5,390,666 A | 2/1995 | Kimm et al. |
| 5,401,135 A | 3/1995 | Stoen et al. |
| 5,402,796 A | 4/1995 | Packer et al. |
| 5,407,174 A | 4/1995 | Kumar |
| 5,413,110 A | 5/1995 | Cummings et al. |
| 5,418,085 A | 5/1995 | Huhndorff et al. |
| 5,438,980 A | 8/1995 | Phillips |
| 5,443,075 A | 8/1995 | Holscher |
| 5,448,152 A | 9/1995 | Albright |
| 5,449,567 A | 9/1995 | Yeh |
| 5,460,901 A | 10/1995 | Syrjala |
| 5,478,665 A | 12/1995 | Burroughs et al. |
| 5,494,051 A * | 2/1996 | Schneider, Sr. ................... 5/625 |
| 5,496,658 A | 3/1996 | Hein et al. |
| 5,513,631 A | 5/1996 | McWilliams |
| 5,514,946 A | 5/1996 | Lin et al. |
| 5,517,983 A | 5/1996 | Deighan et al. |
| 5,520,071 A | 5/1996 | Jones |
| 5,524,615 A | 6/1996 | Power |
| 5,525,439 A | 6/1996 | Huhndorff et al. |
| 5,531,221 A | 7/1996 | Power |
| 5,542,415 A | 8/1996 | Brody |
| 5,544,674 A | 8/1996 | Kelly |
| 5,549,106 A | 8/1996 | Gruenke et al. |
| 5,551,419 A | 9/1996 | Froehlich et al. ......... 128/204.23 |
| 5,567,541 A | 10/1996 | Rouhani |
| 5,596,278 A | 1/1997 | Lin |
| 5,596,984 A | 1/1997 | O'Mahony et al. |
| 5,610,497 A | 3/1997 | Croughwell |
| 5,616,923 A | 4/1997 | Rich et al. |
| 5,630,411 A | 5/1997 | Holscher |
| 5,632,270 A | 5/1997 | O'Mahony et al. |
| 5,635,813 A | 6/1997 | Shiga et al. |
| 5,640,150 A | 6/1997 | Atwater |
| 5,641,587 A | 6/1997 | Mitchell et al. |
| 5,645,048 A | 7/1997 | Brodsky et al. |
| 5,656,919 A | 8/1997 | Proctor et al. |
| 5,660,171 A | 8/1997 | Kimm et al. |
| 5,664,560 A | 9/1997 | Merrick et al. |
| 5,664,562 A | 9/1997 | Bourdon |
| 5,671,767 A | 9/1997 | Kelly |
| 5,672,041 A | 9/1997 | Ringdahl et al. |
| 5,673,689 A | 10/1997 | Power |
| 5,677,077 A | 10/1997 | Faulk |
| 5,693,944 A | 12/1997 | Rich |
| 5,715,812 A | 2/1998 | Deighan et al. |
| 5,738,954 A | 4/1998 | Latella et al. |
| 5,749,374 A * | 5/1998 | Schneider, Sr. ................ 128/870 |
| 5,762,480 A | 6/1998 | Adahan |
| 5,771,884 A | 6/1998 | Yarnall et al. |
| 5,789,100 A | 8/1998 | Burroughs et al. |
| 5,789,660 A | 8/1998 | Kofoed et al. |
| 5,791,339 A | 8/1998 | Winter |
| 5,794,614 A | 8/1998 | Gruenke et al. ............. 128/301 |
| 5,794,986 A | 8/1998 | Gansel et al. |
| 5,813,399 A | 9/1998 | Isaza et al. |
| 5,825,100 A | 10/1998 | Kim |
| 5,826,575 A | 10/1998 | Lall |
| 5,829,441 A | 11/1998 | Kidd et al. |
| 5,861,812 A | 1/1999 | Mitchell et al. |
| 5,864,938 A | 2/1999 | Gansel et al. |
| 5,865,168 A | 2/1999 | Isaza |
| 5,867,007 A | 2/1999 | Kim |
| 5,881,717 A | 3/1999 | Isaza |
| 5,881,723 A | 3/1999 | Wallace et al. |
| 5,884,623 A | 3/1999 | Winter |
| 5,906,204 A | 5/1999 | Beran et al. |
| 5,909,731 A | 6/1999 | O'Mahony et al. |
| 5,915,379 A | 6/1999 | Wallace et al. |
| 5,915,380 A | 6/1999 | Wallace et al. |
| 5,915,382 A | 6/1999 | Power |
| 5,918,597 A | 7/1999 | Jones et al. |
| 5,921,238 A | 7/1999 | Bourdon |
| 5,934,274 A | 8/1999 | Merrick et al. |
| 5,939,799 A | 8/1999 | Weinstein |
| 5,969,429 A * | 10/1999 | Rudolph et al. ................. 290/54 |
| 5,978,236 A | 11/1999 | Faberman et al. |
| 6,024,089 A | 2/2000 | Wallace et al. |
| 6,041,780 A | 3/2000 | Richard et al. |
| 6,045,398 A | 4/2000 | Narita et al. |
| 6,047,860 A | 4/2000 | Sanders |
| 6,054,234 A | 4/2000 | Weiss et al. |
| 6,076,523 A | 6/2000 | Jones et al. |
| 6,084,380 A | 7/2000 | Burton |
| 6,095,140 A | 8/2000 | Poon et al. |
| 6,099,481 A | 8/2000 | Daniels et al. |
| 6,106,480 A | 8/2000 | Gama De Abreu et al. |
| 6,116,240 A | 9/2000 | Merrick et al. |
| 6,116,464 A | 9/2000 | Sanders |
| 6,123,073 A | 9/2000 | Schlawin et al. |
| 6,135,106 A | 10/2000 | Dirks et al. |
| 6,142,150 A | 11/2000 | O'Mahony et al. |
| 6,153,947 A | 11/2000 | Rockow et al. |
| 6,155,986 A | 12/2000 | Brydon et al. |
| 6,156,450 A | 12/2000 | Bailey |
| 6,161,539 A | 12/2000 | Winter |
| 6,179,784 B1 | 1/2001 | Daniels et al. |
| 6,203,502 B1 | 3/2001 | Hilgendorf et al. |
| 6,220,245 B1 | 4/2001 | Takabayashi et al. |
| 6,227,196 B1 | 5/2001 | Jaffe et al. |
| 6,232,782 B1 | 5/2001 | Kacprowicz et al. |
| 6,259,171 B1 | 7/2001 | Cheng |
| 6,269,812 B1 | 8/2001 | Wallace et al. |
| 6,273,444 B1 | 8/2001 | Power |
| 6,283,119 B1 | 9/2001 | Bourdon |
| 6,304,005 B1 | 10/2001 | Aoki et al. |
| 6,305,373 B1 | 10/2001 | Wallace et al. |
| 6,306,098 B1 | 10/2001 | Orr et al. |
| 6,312,389 B1 | 11/2001 | Kofoed et al. |
| 6,321,748 B1 | 11/2001 | O'Mahoney |
| 6,325,785 B1 | 12/2001 | Babkes et al. |
| 6,325,978 B1 | 12/2001 | Labuda et al. |
| 6,330,176 B1 | 12/2001 | Thrap et al. |

(56) References Cited

U.S. PATENT DOCUMENTS

| | | | |
|---|---|---|---|
| 6,357,438 B1 | 3/2002 | Hansen |
| 6,358,215 B1 | 3/2002 | Ricciardelli |
| 6,360,745 B1 | 3/2002 | Wallace et al. |
| 6,369,838 B1 | 4/2002 | Wallace et al. |
| 6,384,491 B1 | 5/2002 | O'Meara |
| 6,390,091 B1 | 5/2002 | Banner et al. |
| 6,394,962 B1 | 5/2002 | Gama De Abreu et al. |
| 6,402,697 B1 | 6/2002 | Calkins et al. |
| 6,408,848 B1 | 6/2002 | Feldman et al. |
| 6,412,483 B1 | 7/2002 | Jones et al. |
| 6,439,229 B1 | 8/2002 | Du et al. |
| 6,467,478 B1 | 10/2002 | Merrick et al. |
| 6,471,658 B1 | 10/2002 | Daniels et al. |
| 6,487,919 B1 * | 12/2002 | Edwards .................... 73/861.77 |
| 6,509,657 B1 | 1/2003 | Wong et al. |
| 6,540,689 B1 | 4/2003 | Orr et al. |
| 6,546,930 B1 | 4/2003 | Emerson et al. |
| 6,553,991 B1 | 4/2003 | Isaza |
| 6,557,553 B1 | 5/2003 | Borrello |
| 6,571,795 B2 | 6/2003 | Bourdon |
| 6,575,164 B1 | 6/2003 | Jaffe et al. |
| 6,603,273 B1 | 8/2003 | Wickham et al. |
| 6,616,896 B2 | 9/2003 | Labuda et al. |
| 6,622,726 B1 | 9/2003 | Du |
| 6,629,934 B2 | 10/2003 | Mault et al. |
| 6,644,310 B1 | 11/2003 | Delache et al. |
| 6,648,831 B2 | 11/2003 | Orr et al. |
| 6,648,832 B2 | 11/2003 | Orr et al. |
| 6,659,962 B2 | 12/2003 | Ricciardelli |
| 6,668,824 B1 | 12/2003 | Isaza et al. |
| 6,675,801 B2 | 1/2004 | Wallace et al. |
| 6,718,974 B1 | 4/2004 | Moberg |
| 6,725,447 B1 | 4/2004 | Gilman et al. |
| 6,739,337 B2 | 5/2004 | Isaza |
| 6,761,167 B1 | 7/2004 | Nadjafizadeh et al. |
| 6,761,168 B1 | 7/2004 | Nadjafizadeh et al. |
| 6,763,829 B2 | 7/2004 | Jaffe et al. |
| 6,802,225 B2 | 10/2004 | Shahar et al. |
| 6,814,074 B1 | 11/2004 | Nadjafizadeh et al. |
| 6,815,211 B1 | 11/2004 | Blazewicz et al. |
| 6,840,906 B2 | 1/2005 | Gama De Abreu et al. |
| 6,866,040 B1 | 3/2005 | Bourdon |
| 6,899,103 B1 | 5/2005 | Hood et al. |
| 6,908,438 B2 | 6/2005 | Orr et al. |
| 6,924,567 B2 | 8/2005 | Killian et al. |
| 6,952,084 B2 | 10/2005 | Bruwer |
| 6,954,702 B2 | 10/2005 | Pierry et al. |
| 6,955,651 B2 | 10/2005 | Kück et al. |
| 6,960,854 B2 | 11/2005 | Nadjafizadeh et al. |
| 6,979,502 B1 | 12/2005 | Gartstein et al. |
| 6,990,980 B2 | 1/2006 | Richey, II |
| 7,004,168 B2 | 2/2006 | Mace et al. |
| 7,005,835 B2 | 2/2006 | Brooks et al. |
| 7,018,340 B2 | 3/2006 | Jaffe et al. |
| 7,032,463 B2 | 4/2006 | Misholi et al. |
| 7,036,504 B2 | 5/2006 | Wallace et al. |
| 7,066,176 B2 | 6/2006 | Jaffe et al. |
| 7,074,196 B2 | 7/2006 | Kück et al. |
| 7,077,131 B2 | 7/2006 | Hansen |
| 7,080,646 B2 | 7/2006 | Wiesmann et al. |
| RE39,225 E | 8/2006 | Isaza et al. |
| 7,089,930 B2 | 8/2006 | Adams et al. ............. 128/201.27 |
| 7,101,341 B2 | 9/2006 | Tsukashima et al. ......... 600/532 |
| 7,117,438 B2 | 10/2006 | Wallace et al. |
| 7,135,001 B2 | 11/2006 | Orr et al. |
| 7,183,552 B2 | 2/2007 | Russell |
| RE39,703 E | 6/2007 | Burroughs et al. |
| 7,252,088 B1 | 8/2007 | Nieves Ramirez |
| 7,268,660 B2 | 9/2007 | Bolda et al. |
| 7,270,126 B2 | 9/2007 | Wallace et al. |
| 7,291,851 B2 | 11/2007 | DelFavero et al. |
| 7,297,120 B2 | 11/2007 | Tsukashima et al. ......... 600/532 |
| 7,320,321 B2 | 1/2008 | Pranger et al. |
| 7,335,164 B2 | 2/2008 | Mace et al. |
| 7,339,350 B2 | 3/2008 | Kubale et al. |
| 7,341,563 B2 | 3/2008 | Rich et al. |
| 7,347,205 B2 | 3/2008 | Levi |
| 7,369,757 B2 | 5/2008 | Farbarik |
| 7,370,650 B2 | 5/2008 | Nadjafizadeh et al. |
| RE40,506 E | 9/2008 | Burroughs et al. |
| 7,427,269 B2 | 9/2008 | George et al. |
| 7,428,902 B2 | 9/2008 | Du et al. |
| 7,432,508 B2 | 10/2008 | Daniels et al. |
| 7,460,959 B2 | 12/2008 | Jafari |
| 7,487,773 B2 | 2/2009 | Li |
| 7,509,957 B2 | 3/2009 | Duquette et al. |
| 7,607,360 B2 | 10/2009 | Todokoro et al. |
| 7,654,802 B2 | 2/2010 | Crawford, Jr. et al. |
| 7,658,891 B1 * | 2/2010 | Barnes .................... 422/186.03 |
| 7,694,677 B2 | 4/2010 | Tang |
| 7,717,113 B2 | 5/2010 | Andrieux |
| 7,721,736 B2 | 5/2010 | Urias et al. |
| 7,741,815 B2 | 6/2010 | Cassidy |
| 7,784,461 B2 | 8/2010 | Figueiredo et al. |
| 7,823,588 B2 | 11/2010 | Hansen |
| 7,855,716 B2 | 12/2010 | McCreary et al. |
| D632,796 S | 2/2011 | Ross et al. |
| D632,797 S | 2/2011 | Ross et al. |
| 7,891,354 B2 | 2/2011 | Farbarik |
| 7,893,560 B2 | 2/2011 | Carter |
| 7,984,714 B2 | 7/2011 | Hausmann et al. |
| 7,985,254 B2 * | 7/2011 | Tolkowsky ...................... 623/9 |
| 7,992,557 B2 | 8/2011 | Nadjafizadeh et al. |
| 8,001,967 B2 | 8/2011 | Wallace et al. |
| 8,021,310 B2 | 9/2011 | Sanborn et al. |
| 8,181,648 B2 | 5/2012 | Perine et al. |
| 8,210,173 B2 | 7/2012 | Vandine |
| 8,210,174 B2 | 7/2012 | Farbarik |
| 8,267,085 B2 | 9/2012 | Jafari et al. |
| 8,272,379 B2 | 9/2012 | Jafari et al. |
| 8,272,380 B2 | 9/2012 | Jafari et al. |
| 8,302,600 B2 | 11/2012 | Andrieux et al. |
| 8,302,602 B2 | 11/2012 | Andrieux et al. |
| 2001/0011845 A1 | 8/2001 | Simonelli et al. |
| 2001/0029339 A1 | 10/2001 | Orr et al. |
| 2001/0031928 A1 | 10/2001 | Orr et al. |
| 2002/0116994 A1 | 8/2002 | Heinonen |
| 2002/0128566 A1 | 9/2002 | Gama De Abreu et al. |
| 2003/0047188 A1 | 3/2003 | Mace et al. |
| 2003/0191405 A1 | 10/2003 | Rich et al. |
| 2004/0015058 A1 | 1/2004 | Besson et al. ............. 600/201.27 |
| 2004/0087867 A1 | 5/2004 | Gama De Abreu et al. |
| 2004/0118403 A1 | 6/2004 | O'Connor et al. ....... 128/204.23 |
| 2004/0186391 A1 | 9/2004 | Pierry et al. |
| 2004/0256560 A1 | 12/2004 | Russell |
| 2005/0039748 A1 | 2/2005 | Andrieux |
| 2005/0052085 A1 | 3/2005 | Chang et al. |
| 2005/0139212 A1 | 6/2005 | Bourdon |
| 2005/0217275 A1 * | 10/2005 | Hendrickson et al. .......... 60/775 |
| 2005/0279358 A1 | 12/2005 | Richey, II |
| 2005/0285055 A1 | 12/2005 | DelFavero et al. |
| 2006/0009707 A1 | 1/2006 | Daniels et al. |
| 2006/0052950 A1 | 3/2006 | Pierry et al. |
| 2006/0086357 A1 | 4/2006 | Soliman et al. |
| 2006/0129054 A1 | 6/2006 | Orr et al. |
| 2006/0145078 A1 | 7/2006 | Russell |
| 2006/0162728 A1 | 7/2006 | Delache et al. .......... 128/204.22 |
| 2006/0241508 A1 | 10/2006 | Jaffe et al. |
| 2006/0249153 A1 | 11/2006 | DeVries et al. |
| 2006/0253038 A1 | 11/2006 | Kuck et al. |
| 2007/0017515 A1 | 1/2007 | Wallace et al. |
| 2007/0044798 A1 | 3/2007 | Levi |
| 2007/0077200 A1 | 4/2007 | Baker |
| 2007/0100222 A1 | 5/2007 | Mastrototaro et al. |
| 2007/0107728 A1 | 5/2007 | Ricciardelli et al. |
| 2007/0142716 A1 | 6/2007 | Biondi |
| 2007/0149891 A1 | 6/2007 | George et al. |
| 2007/0152630 A1 | 7/2007 | Winkler et al. |
| 2007/0157930 A1 | 7/2007 | Soliman et al. |
| 2007/0199566 A1 | 8/2007 | Be'eri |
| 2007/0227537 A1 | 10/2007 | Bemister et al. |
| 2007/0272241 A1 | 11/2007 | Sanborn et al. |
| 2007/0272242 A1 | 11/2007 | Sanborn et al. |
| 2007/0273216 A1 | 11/2007 | Farbarik |

(56) References Cited

U.S. PATENT DOCUMENTS

| | | |
|---|---|---|
| 2007/0273887 A1 | 11/2007 | Russell |
| 2007/0282214 A1 | 12/2007 | George et al. |
| 2007/0284361 A1 | 12/2007 | Nadjafizadeh et al. |
| 2008/0021339 A1 | 1/2008 | Gabriel et al. |
| 2008/0053441 A1 | 3/2008 | Gottlib et al. |
| 2008/0058667 A1 | 3/2008 | Pierry et al. |
| 2008/0072896 A1 | 3/2008 | Setzer et al. |
| 2008/0072902 A1 | 3/2008 | Setzer et al. |
| 2008/0078390 A1 | 4/2008 | Milne et al. |
| 2008/0083644 A1 | 4/2008 | Janbakhsh et al. |
| 2008/0091117 A1 | 4/2008 | Choncholas et al. |
| 2008/0092894 A1 | 4/2008 | Nicolazzi et al. |
| 2008/0092898 A1 | 4/2008 | Schneider et al. ....... 128/206.28 |
| 2008/0097234 A1 | 4/2008 | Nicolazzi et al. |
| 2008/0119753 A1 | 5/2008 | Ricciardelli et al. |
| 2008/0167614 A1 | 7/2008 | Tolkowsky et al. |
| 2008/0177404 A1 | 7/2008 | Bonnat .......................... 700/90 |
| 2008/0200776 A1 | 8/2008 | Schermeier et al. .......... 600/301 |
| 2008/0302172 A1* | 12/2008 | Kates ........................ 73/40.5 R |
| 2009/0044805 A1 | 2/2009 | Somaiya et al. |
| 2009/0165795 A1 | 7/2009 | Nadjafizadeh et al. |
| 2009/0171176 A1 | 7/2009 | Andersohn |
| 2009/0205661 A1 | 8/2009 | Stephenson et al. |
| 2009/0205663 A1 | 8/2009 | Vandine et al. |
| 2009/0241952 A1 | 10/2009 | Nicolazzi et al. |
| 2009/0241953 A1 | 10/2009 | Vandine et al. |
| 2009/0241956 A1 | 10/2009 | Baker, Jr. et al. |
| 2009/0241957 A1 | 10/2009 | Baker, Jr. |
| 2009/0241958 A1 | 10/2009 | Baker, Jr. |
| 2009/0241962 A1 | 10/2009 | Jafari et al. |
| 2009/0247891 A1 | 10/2009 | Wood |
| 2009/0301486 A1 | 12/2009 | Masic |
| 2009/0301487 A1 | 12/2009 | Masic |
| 2009/0301490 A1 | 12/2009 | Masic |
| 2009/0301491 A1 | 12/2009 | Masic et al. |
| 2009/0320842 A1* | 12/2009 | Doherty et al. .......... 128/204.21 |
| 2010/0011307 A1 | 1/2010 | Desfossez et al. |
| 2010/0024820 A1 | 2/2010 | Bourdon |
| 2010/0071689 A1 | 3/2010 | Thiessen |
| 2010/0071695 A1 | 3/2010 | Thiessen |
| 2010/0071696 A1 | 3/2010 | Jafari |
| 2010/0078017 A1 | 4/2010 | Andrieux et al. |
| 2010/0078026 A1 | 4/2010 | Andrieux et al. |
| 2010/0081119 A1 | 4/2010 | Jafari et al. |
| 2010/0081955 A1 | 4/2010 | Wood, Jr. et al. |
| 2010/0104929 A1 | 4/2010 | Schäfer et al. |
| 2010/0139660 A1 | 6/2010 | Adahan |
| 2010/0147303 A1 | 6/2010 | Jafari et al. |
| 2010/0218765 A1 | 9/2010 | Jafari et al. |
| 2010/0218766 A1 | 9/2010 | Milne |
| 2010/0218767 A1 | 9/2010 | Jafari et al. |
| 2010/0236555 A1 | 9/2010 | Jafari et al. |
| 2010/0242961 A1 | 9/2010 | Mougel et al. |
| 2010/0253288 A1 | 10/2010 | Cassidy |
| 2010/0288283 A1 | 11/2010 | Campbell et al. |
| 2010/0300446 A1 | 12/2010 | Nicolazzi et al. |
| 2011/0023879 A1 | 2/2011 | Vandine et al. |
| 2011/0162647 A1* | 7/2011 | Huby et al. .............. 128/203.14 |
| 2011/0259330 A1 | 10/2011 | Jafari et al. |
| 2012/0053431 A1 | 3/2012 | Mannheimer et al. ........ 600/323 |

FOREIGN PATENT DOCUMENTS

| | | |
|---|---|---|
| FR | 2829942 A1 | 3/2003 |
| JP | 2002136595 | 5/2002 |
| WO | 90/04425 | 5/1990 |
| WO | WO 96/17425 | 8/1996 |
| WO | WO 96/41571 | 12/1996 |
| WO | WO 98/34314 | 8/1998 |
| WO | 2006138578 A2 | 12/2006 |

OTHER PUBLICATIONS

"GoodKnight® 425 GoodKnight® 425ST Clinician and Home Care Provider Manual", Puritan Bennett, Revision G, p. 25, referring to breathing circuits having an "internal pressure sensor line", Mar. 2010.

"Puritan Bennett CPAP / BiLEVEL Tubing with Internal Pressure Sensor Line", Printout of page from website www.cpapxchange.com, 2 pages, Printed Jun. 9, 2010.

International PCT Search Report and Written Opinion, PCT/US2009/055288, 17 pages, Mailed Dec. 4, 2009.

Application for Letters Patent, "System and Process for Supplying Respiratory Gas Under Pressure or Volumetrically," Inventor Claude Andreiux, 21 pages, Filed Jul. 27, 2004.

7200 Series Ventilator, Options, and Accessories: Operator's Manual. Nellcor Puritan Bennett, Part No. 22300 A, Sep. 1990, pp. 1-196.

7200 Ventilatory System: Addendum/Errata. Nellcor Puritan Bennett, Part No. 4-023576-00, Rev. A, Apr. 1998, pp. 1-32.

800 Operator's and Technical Reference Manual. Series Ventilator System, Nellcor Puritan Bennett, Part No. 4-070088-00, Rev. L, Aug. 2010, pp. 1-476.

840 Operator's and Technical Reference Manual. Ventilator System, Nellcor Puritan Bennett, Part No. 4-075609-00, Rev. G, Oct. 2006, pp. 1-424.

\* cited by examiner

US 8,776,790 B2

WIRELESS, GAS FLOW-POWERED SENSOR SYSTEM FOR A BREATHING ASSISTANCE SYSTEM

TECHNICAL FIELD

The present disclosure relates generally to the field of medical devices, e.g., wireless, gas flow-powered sensor system for a breathing assistance system (e.g., a ventilator or CPAP system).

BACKGROUND

Conventional breathing assistance systems typically include a gas delivery system (e.g., a ventilator, CPAP device, etc.), a patient interface (e.g., nasal mask, face mask, nasal pillows, endotrachael tube, etc.) to deliver gas to one or more breathing passages of the patient, and a connection system (e.g., patient circuit) between the gas delivery system and the patient interface. Such breathing assistance systems may be used, e.g., for mechanical ventilation of a patient's lungs and/or treatment of an apnea or other medical condition.

Some breathing assistance systems include one or more sensors for measuring parameters related to the patient (e.g., the patient's breath rate, heart rate, etc.), the gas flow delivered to the patient (e.g., the flow rate, pressure, etc.), and/or various other parameters. In some systems, sensor(s) for measuring parameters at the patient end of the system are located at or near the patient interface (e.g., nasal mask) and physically connected to a control unit of the gas delivery system by wires running through or integrated with the patient circuit. In other systems, sensor(s) for measuring parameters at the patient end of the system are located at or near the gas delivery system, and algorithms are applied to the sensor measurements in order to approximate the measurements of such parameters at the patient end of the system (e.g., to correct for the pressure drop that occurs between the gas delivery system and the patient).

SUMMARY

In some embodiments of the present disclosure, a breathing assistance system for providing breathing assistance to a patient includes a gas delivery system configured to generate a gas flow, a patient interface configured to interface with the patient, a connection system connected between the gas delivery system and the patient interface and configured to communicate the gas flow to the patient interface for delivery to the patient, and a sensor system remote from the gas delivery system and connected to at least one of the patient interface and the connection system. The sensor system includes a sensor for measuring a parameter, a turbine configured to be driven by the gas flow, and an electrical generator coupled to the turbine and configured to generate electricity for powering the sensor.

In some embodiments of the present disclosure, a sensor system is provided for use in a breathing assistance system including a gas delivery system configured to generate a gas flow, a patient interface configured to interface with the patient, and a connection system connected between the gas delivery system and the patient interface and configured to communicate the gas flow to the patient interface for delivery to the patient. The sensor system includes a sensor for measuring a parameter, a turbine configured to be driven by the gas flow, and an electrical generator coupled to the turbine and configured to generate electricity for powering the sensor. The sensor system is located remote from the gas delivery system and connected to at least one of the patient interface and the connection system.

In some embodiments of the present disclosure, a method is provided for operating a sensor system in a breathing assistance system including a gas delivery system configured to generate a gas flow, a patient interface configured to interface with the patient, and a connection system connected between the gas delivery system and the patient interface and configured to communicate the gas flow to the patient interface for delivery to the patient. The method includes providing a turbine configured to be activated by the gas flow, generating an electrical current from the turbine activated by the gas flow, and powering a sensor using the electrical current generated from the turbine. In some embodiments, sensor signals detected by the sensor may be wirelessly communicated to a control system associated with the gas delivery system such that the control system can adjust the gas flow generated by the gas delivery system based at least on the sensor signals.

In some embodiments of the present disclosure, a breathing assistance system for providing breathing assistance to a patient includes a gas delivery system configured to generate a gas flow, a patient interface configured to interface with the patient, a connection system connected between the gas delivery system and the patient interface and configured to communicate the gas flow to the patient interface for delivery to the patient, and a sensor system remote from the gas delivery system and connected to at least one of the patient interface and the connection system. The sensor system includes a sensor for measuring a parameter, and a solar power device configured to convert light energy into electricity for powering the sensor.

BRIEF DESCRIPTION OF THE DRAWINGS

Some embodiments of the disclosure may be understood by referring, in part, to the following description and the accompanying drawings wherein.

DETAILED DESCRIPTION OF THE DRAWINGS

Figure 1:
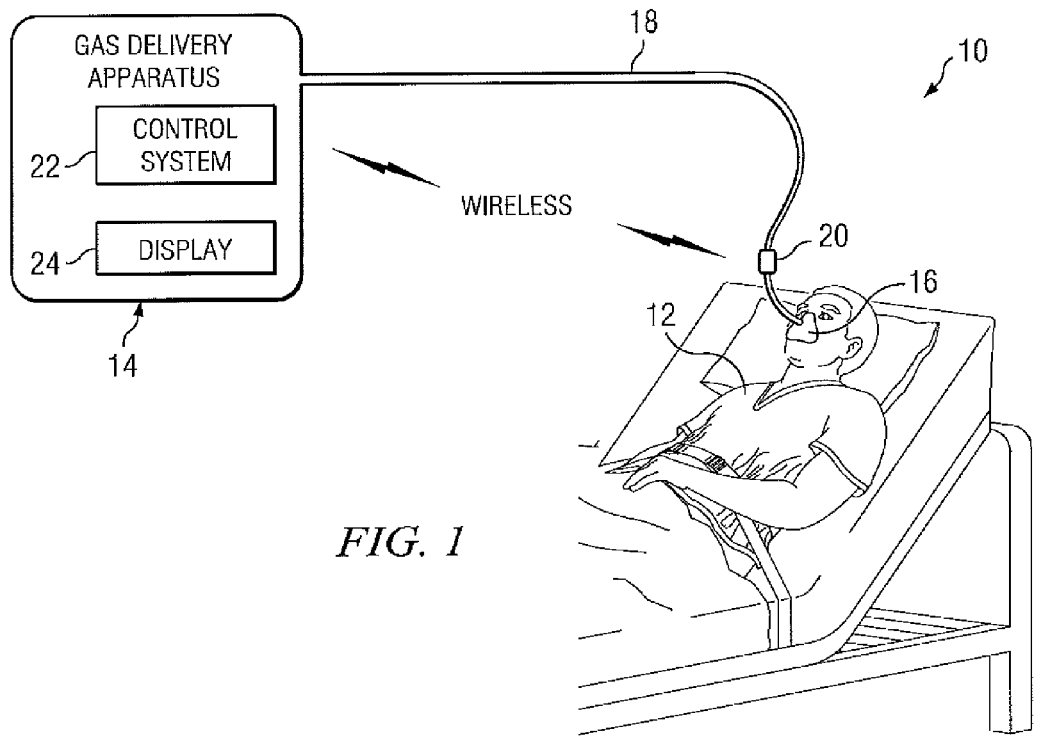
FIG. 1 illustrates an example breathing assistance system for providing breathing assistance to a patient, including a sensor system powered by a gas flow of the breathing assistance system, according to certain embodiments of the disclosure.

Selected embodiments of the disclosure may be understood by reference, in part, to FIGS. 1-9, wherein like numbers refer to same and like parts. The present disclosure is broadly concerned with breathing assistance systems (e.g., ventilators, CPAP systems, or BiPAP systems) having a sensor system that is powered by a gas flow of the respective breathing assistance system. The sensor system may be wirelessly connected to a display and/or control system for controlling parameter(s) of the breathing assistance system (e.g.) the gas flow rate, pressure, etc. of the gas flow to the patient).

In some embodiments, a breathing assistance system for providing breathing assistance to a patient includes a gas delivery system (e.g., a ventilator or CPAP device) configured to generate a gas flow, a patient interface (e.g., a nasal mask, face mask, or nasal pillows) configured to interface with the patient, a connection system (e.g., a patient circuit) connected between the gas delivery system and the patient interface and configured to communicate the gas flow to the patient interface for delivery to the patient. A sensor system may be located remote from the gas delivery system, e.g., connected to at least one of the patient interface and the connection system. The sensor system may include one or more sensors for measuring one or more parameters, a turbine driven by the gas flow from the gas delivery system, and an electrical generator configured to generate electricity from the gas flow-driven turbine. The turbine may extend at least partially into the patient interface and/or connection system to receive the gas flow, or may be otherwise arranged in relation to the patient interface and/or connection system to receive the gas flow.

The electricity generated by the generator may be delivered directly to the sensor(s), or may be delivered to an electrical charge storage device, e.g., battery or a capacitor, for subsequent delivery to the sensor(s). In this manner, the sensor system may be independently powered, which may allow the sensor system to be used with various standard or off-the-shelf patient interfaces and/or patient circuits.

In some embodiments, the sensor system may also include a voltage regulator for regulating the voltage output by the generator. The voltage regulator may include, for example, one or more diodes, a shunt, and/or any other suitable components. The sensor system may also include a signal processing unit for processing sensor signals received from the sensor(s) such that the signals may be displayed and/or transmitted.

As discussed above, in some embodiments, the sensor system may be wirelessly connected to a display and/or control system. Accordingly, the sensor system may include a wireless transmitter, receiver, and/or transceiver for wirelessly communicating sensor signals (either unprocessed or processed by a signal processing unit), commands, and/or other suitable data between the sensor system and a display and/or control system.

The sensor system may be connected to the breathing assistance system at and suitable location and in any suitable manner. For example, the sensor system may be permanently integrated with, or removably connected to, the patient interface, the connection system, or both. In some embodiments the sensor system is connected in series between the patient interface and the connection system.

FIG. 1 illustrates an example breathing assistance system 10 for providing breathing assistance to a patient 12, according to one embodiment of the disclosure. Breathing assistance system 10 may be generally configured to provide breathing assistance (e.g., providing ventilation and/or treating an apnea or other breathing condition) to a patient 12. Breathing assistance system 10 may include a gas delivery apparatus 14, a patient interface 16, a connection system 18 between gas delivery apparatus 14 and patient interface 16, and a sensor system 20 for measuring one or more parameters associated with breathing assistance system 10 and/or patient 12, sensor system 20 being powered by a gas flow generated by gas delivery apparatus 14.

Gas delivery apparatus 14 may include any device or devices configured to generate, supply, and/or deliver gas (e.g., pressurized air) toward patient 12 via patient interface 16. For example, gas delivery apparatus 14 may comprise a device capable of generating pressurized air (e.g., a ventilator, CPAP system, or BiPAP system), a wall outlet through which pressurized air may be supplied (e.g., in a hospital or clinic), one or more tanks of compressed gas, a compressor, or any other suitable source of pressurized or non-pressurized gas.

As used herein, the term "gas" may refer to any one or more gases and/or vaporized substances suitable to be delivered to and/or from a patient via one or more breathing orifices (e.g., the nose and/or mouth), such as air, nitrogen, oxygen, any other component of air, $CO_2$, vaporized water, vaporized medicines, and/or any combination of two or more of the above, for example. As used herein, the term "patient" may refer to any person or animal that may receive breathing assistance from system 10, regardless of the medical status, official patient status, physical location, or any other characteristic of the person. Thus, for example, patients may include persons under official medical care (e.g., hospital patients), persons not under official medical care, persons receiving care at a medical care facility, persons receiving home care, etc.

Gas delivery apparatus 14 may include a gas delivery control system 22 operable to control the breathing assistance provided by gas delivery apparatus 14 based on various input. For example, gas delivery control system 22 may regulate the pressure and/or flow of gas delivered to patient 12 based on various input (e.g., data received from sensors and/or input from a user). Gas delivery control system 22 may include, or have access to, one or more processors, memory devices, and any other suitable hardware or software. The one or more memory devices may store instructions (e.g., any suitable software, algorithms, or other logic or instructions that may be executed by one or more processors) for controlling the operation of gas delivery apparatus 14, e.g., controlling ventilation support provided by gas delivery apparatus 14.

Gas delivery apparatus 14 may also include one or more display devices 24 for displaying various information regarding system 10 (e.g., data regarding patient 12, the operation of gas delivery apparatus 14, and/or any other relevant data). In some embodiments, display device(s) 24 may be configured to display sensor signals (e.g., measured values) received wirelessly from sensor system 20. Alternatively, or in addition, sensor signals from sensor system 20 may be displayed on a display at sensor system 20 or on a mobile display device (e.g., a mobile handheld device), as discussed below.

Gas delivery apparatus 14 may further include any other components suitable for providing functionality related to providing breathing assistance to a patient 12. For example, gas delivery apparatus 14 may include one or more sensors, a humidifier, a nebulizer, an alarm system, and/or any other suitable components.

Patient interface 16 may include any device or devices configured to interface with patient 12 to deliver gas to patient 12. For example, patient interface 16 may include a mask (e.g., a nasal mask or face mask) or nasal pillows positioned over the patient's nose and/or mouth, a patient connection tube directly connected to the patient's trachea, or an artificial airway (e.g., an endotracheal tube or other device) inserted in the patient's trachea. In embodiments including a patient connection tube, the patient connection tube may include a wye (or "Y") connector.

Connection system 18 may include any suitable means for connecting gas delivery apparatus 14 to patient interface 16. Connection system 18 may include one or more tubes, hoses, or other conduits suitable to communicate gas. Such tubes, hoses, or other conduits may be formed from any suitable materials, e.g., plastic, rubber, or other polymers, and may be generally flexible or generally rigid. For example, connection system 18 may comprise a patient circuit (sometimes referred to as a breathing circuit) including a flexible inspiration conduit and/or a flexible exhalation conduit. In some embodiments, connection system 18 may comprise a single-limb or a dual-limb patient circuit.

When assembled, system 10 may define one or more gas delivery passageways from gas delivery apparatus 14, through connection system 18, and through patient interface 16. Such passageways may be used to deliver gas from gas delivery apparatus 14 to patient 12. In addition, in some embodiments, patient interface 16 and/or connection system 18 may include or define one or more passageways for communicating exhaled gas away from patient 12.

Sensor system 20 is configured to measure one or more parameters associated with breathing assistance system 10 and/or patient 12. Sensor system 20 is powered by a gas flow generated by gas delivery apparatus 14. In some embodiments, sensor system 20 may wirelessly communicate signals for processing and/or display, as discussed below in greater detail.

Figure 2:
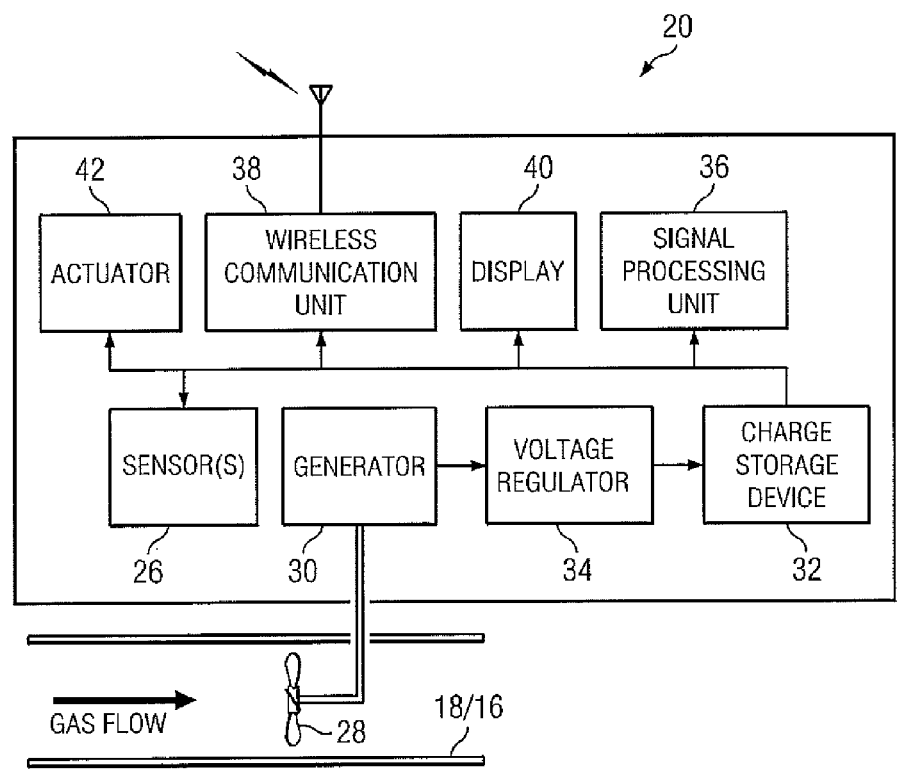
FIG. 2 illustrates various components of an example sensor system for use in the breathing assistance system of FIG. 1, according to certain embodiments.

FIG. 2 illustrates various components of sensor system 20, according to example embodiments. Sensor system 20 may include one or more sensors 26, a turbine 28, and an electrical generator 30. In some embodiments, sensor system 20 may also include any or all of an electrical charge storage device 32, a voltage regulator 34, a signal processing unit 36, a wireless communication unit 38, a display 40, and one or more actuators 42.

Sensors 26 may include any device or devices for sensing, detecting, and/or monitoring one or more parameters related to the breathing assistance provided to patient 12, e.g., parameters regarding the operation of gas delivery apparatus 14 and/or physiological parameters regarding patient 12. For example, sensors 26 may include one or more devices for measuring various parameters of gas flowing into or out of patient 12 or gas delivery apparatus 14, e.g., the pressure, flow rate, flow volume, temperature, gas content, and/or humidity of such gas flow. Thus, sensors 26 may include, e.g., one or more pressure sensors, flow meters, transducers, and/or oxygen sensors.

In certain embodiments, sensors 26 be configured to measure or sample one or more of the following:

(a) Pressure information: this information can be used by breathing assistance system 10 for pressure regulation, respiratory events detection, pneumatic resistance qualification of patient interface 16, for the recording of observance data, etc.

(b) Flow information: this information can be used by breathing assistance system 10 for pressure regulation, respiratory events detection, pneumatic resistance qualification of the patient interface 16, for the recording of observance data, etc.

(c) Humidity information: this information can be used by breathing assistance system 10 and for humidity regulation) for recording of observance data, etc.

(d) Temperature information: this information can be used by breathing assistance system 10 for humidity regulation, for patient safety with a high temperature alarm, for the recording of observance data, etc.

Sensor system 20 including sensor(s) 26 may be located at one or more various locations in breathing assistance system 10 for monitoring the pressure and or flow of gasses flowing into and/or out of patient 12 and/or gas delivery apparatus 14. For example, sensor system 20 may be integrated with or located in or proximate gas delivery apparatus 14, connection system 18, and/or patient interface 16.

In some embodiments, sensor system 20 including sensor (s) 26 may be at least partially integrated with or otherwise coupled to patient interface 16 or the patient end of connection system 18, to provide access to patient parameters (e.g., core temperature, tracheal pressure, tissue pH, and/or other measurable parameters). For example, in embodiments in which patient interface 16 comprises a tracheal tube, an oro/naso tracheal tube and/or a mask, one or more sensors 26 (e.g., a thermistor, a pH electrode and/or a pressure transducer) may be integrated with or located in or proximate the tube or mask. Example configurations include, but are not limited to, sensors 26 integrated within a sidewall of patient interface 16, secured to the internal or external surface of a sidewall of patient interface 16, and/or attached or otherwise associated with any component of patient interface 16 and/or connection system 18.

Turbine 28 and electrical generator 30 cooperate to generate electricity based on a gas flow acting on turbine 28. Turbine 28 may comprise one or more blades or rotors driven by the gas flow, and electrical generator 30 generates electricity from the rotating turbine 28. Turbine 28 may be located and oriented in any suitable manner for receiving a gas flow. For example, turbine 28 may extend directly into the main flow path from gas delivery apparatus 14 to patient 12 to receive the gas flow. As another example, a secondary conduit extending off the main flow path may be provided for housing turbine 28, e.g., to reduce effects in the gas flow caused by turbine 28.

In some embodiments, a substantially rigid housing may be provided for housing turbine 28. The housing may include one or more walls, flanges, baffles, or other structures for directing a desired portion of the gas flow to turbine 28. The housing may also include an exhaust outlet to promote a flow of gas through turbine 28.

In some embodiments, turbine 28 and sensor(s) 26 may be positioned to interface with different areas of the gas flow such that turbine 28 does not significantly affect the parameter readings of sensor(s) 26. For example, sensor(s) 26 may be located upstream from turbine 28 to reduce the effects of turbine 28 on the sensor measurements. As another example, one or more walls, flanges, baffles, or other structures may be used to separate the portions of the gas flow acting on turbine 28 and sensor(s) 26. As another example, one of turbine 28 and sensor(s) 26 may extend into the main gas flow path from gas delivery apparatus 14 to patient 12, while the other may be located in a secondary conduit extending off the main flow path.

Example configurations of turbine 28 and sensors 26 are shown in FIGS. 3-6, which are discussed below in greater detail.

Turbine 28 and electrical generator 30 may comprise any suitable type, size, and/or capacity of turbine/generator for providing the functions discussed herein. For example, turbine 28 and electrical generator 30 may provide power to each load of sensor system 20, including sensors 26, signal processing unit 36, wireless communication unit 38, display 40, and/or actuator(s) 42. In a particular embodiment, turbine 28 and electrical generator 30 may be configured to produce approximately 3 volts or 0.02 Amps based on a flow rate of 15 LPM.

Voltage regulator 34 may include any devices and/or circuitry for regulating the voltage output by electrical generator 30. Voltage regulator 34 may include, for example, one or more diodes, a shunt, and/or any other suitable components.

Electrical charge storage device 32 may include any devices and/or circuitry for storing electricity generated by electrical generator 30. For example, electrical charge storage device 32 may include one or more capacitors or batteries, e.g., rechargeable Lithium-ion button cells (example dimensions: diameter=12.5 mm, height=3 mm).

In some embodiments, system 20 may be maintained in a sleep or very low-power mode and awakened only upon a triggering event (e.g., an interrupt generated by a timer or a command signal received from a user input on system 20 or wirelessly received from gas delivery control system 22) to perform one or more power-requiring tasks (e.g., taking a sensor measurement, processing sensor signals, wirelessly communicating signals, displaying signals). Accordingly, in some embodiments, electrical charge storage device 32 (or another component of system 20) may include a timer configured to periodically generate an interrupt signal that triggers one or more power-requiring tasks. In this manner, the power requirements of system 20 may be greatly reduced.

Signal processing unit 36 may include any devices and/or circuitry (hardware, firmware, and/or software) for processing sensor signals received from sensor(s) 26 such that the signals may be displayed and/or transmitted, e.g., by wireless communication unit 38. For example, signal processing unit 36 may be configured for converting analog signals to digital signals and/or converting signals to values (e.g., parameter measurements). As another example, signal processing unit 36 may be configured for processing signals (e.g., heartbeat or command signals) received wirelessly from gas delivery control system 22. For example, signal processing unit 36 may process a command signal from gas delivery control system 22 instructing sensor system 20 to take a measurement. Signal processing unit 36 may also include a memory device for storing unprocessed or processed signals.

Wireless communication unit 38 may include any devices and/or circuitry (hardware, firmware, and/or software) for wirelessly communicating (transmitting, receiving, or both) data between sensor system 20 and one or more remote devices, e.g., gas delivery control system 22, display device 24, a mobile display device 60, or any other suitable device. For example, wireless communication unit 38 may be configured to transmit unprocessed signals from sensor(s) 26, or processed signals from signal processing unit 36, to a wireless receiver of gas delivery control system 22, display device 24, etc. As another example, wireless communication unit 38 may be configured to receive data, e.g., commands or heartbeat signals, from gas delivery control system 22. Wireless communication unit 38 may support any suitable type(s) of wireless communication, for example Wi-Fi, Bluetooth, RFID, infra-red, HF (e.g., ISM band), etc.

As discussed above, gas delivery control system 22 may be operable to control the ventilation support provided by gas delivery apparatus 14 based on various input. Such input may include sensor signals received from wireless communication unit 38 of sensor system 20. For example, gas delivery control system 22 may regulate the pressure, flow, and/or any other parameter of breathing gas delivered to patient 12 based at least on sensor signals received wirelessly from sensor system 20 indicating one or more parameters, e.g., pressure, flow, temperature, humidity, pH, and/or any other relevant parameter.

Display 40 may comprise any device or devices operable to display data (e.g., sensor readings processed by signal processing unit 36) in any suitable format, e.g., numerical values, graphs, etc. Display 40 may be physically integrated with, or connected to a housing of sensor system 20.

Each actuator 42 may comprise any actuator or other electromechanical element to perform any suitable mechanical or electromechanical functions related to system 10. For example, one or more actuators 42 may be configured to control one or more components of system 10, such as controlling a valve (e.g., an anti-return valve, a non-return valve, a pressure discharge valve, or a gas-mixture control valve), triggering a safety system (e.g., triggering an alarm or shutting off gas delivery apparatus 14), etc.

Figure 3:
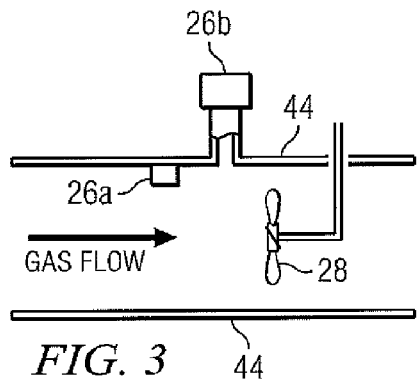
FIGS. 3-6 illustrate example configurations of a turbine and sensors positioned in a breathing assistance system, according to certain embodiments.

FIG. 3 illustrates a first example configuration in which turbine 28 is positioned in the main gas flow path from gas delivery apparatus 14 to patient 12, defined by walls 44, and one or more sensors 26 are positioned upstream from turbine 28. Walls 44 may be the walls of a conduit of connection system 18 (e.g., a patient circuit), the walls of a patient interface 16 (e.g., a tube or mask), a housing inserted at least partially within or integrated with connection system 18 and/or patient interface 16, or a housing connected between connection system 18 and patient interface 16. In some embodiments, walls 44 may form a substantially rigid housing for turbine 28 and/or sensors 26. Any suitable number and types of sensors 26 may be provided. For example, two types of sensors 26 are shown in the configuration of FIG. 3: a first type of sensor 26a (e.g., a type of flow rate or temperature sensor) positioned within the main flow path, and a second type of sensor 26b (e.g., a type of pressure sensor) that includes at least one passage extending off the main flow path.

Figure 4:
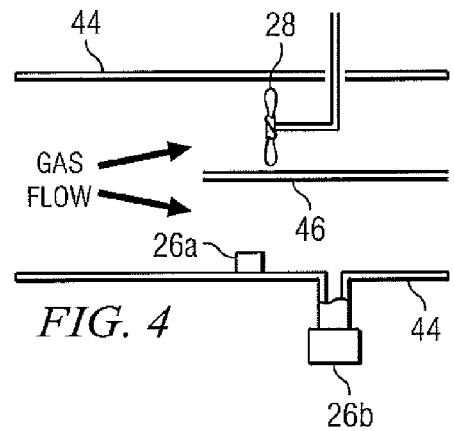

FIG. 4 illustrates a second example configuration in which turbine 28 is positioned in the main gas flow path, again defined by walls 44, and separated from one or more sensors 26 (again illustrated by example sensors 26a and 26b) by one or more walls, flanges, baffles, or other structures 46. Such structure(s) 46 may direct desired portions of the gas flow to turbine 28 and/or sensor(s) 26, and/or reduce the effects of turbine 28 on the sensor measurements.

Figure 5:
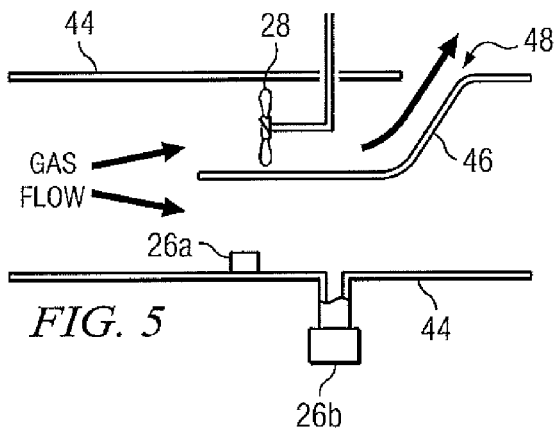

FIG. 5 illustrates a third example configuration in which turbine 28 is positioned in the main gas flow path, again defined by walls 44, and one or more sensors 26 (again illustrated by example sensors 26a and 26b) are positioned upstream from turbine 28. A housing at least partially defined by one or more walls, flanges, baffles, or other structures 46 is provided to direct a desired portion of the gas flow to turbine 28. The housing may also include an exhaust outlet 48 to promote a flow of gas through turbine 28.

Figure 6:
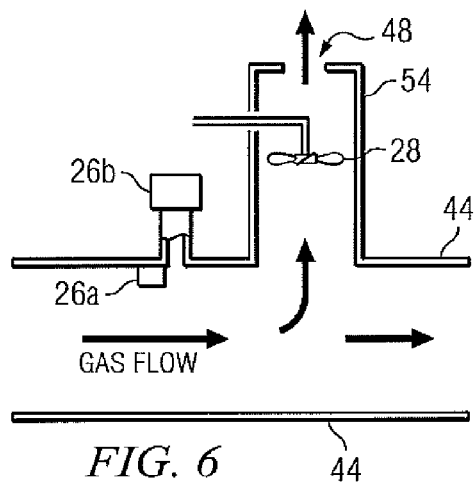

FIG. 6 illustrates a fourth example configuration in which turbine 28 is positioned in a substantially rigid housing 54 extending off the main gas flow path, and one or more sensors 26 (again illustrated by example sensors 26a and 26b) positioned along the main flow path upstream from turbine 28. Housing 54 directs a desired portion of the gas flow to turbine 28, and includes an exhaust outlet 48 to promote a flow of gas through turbine 28.

Figure 7:
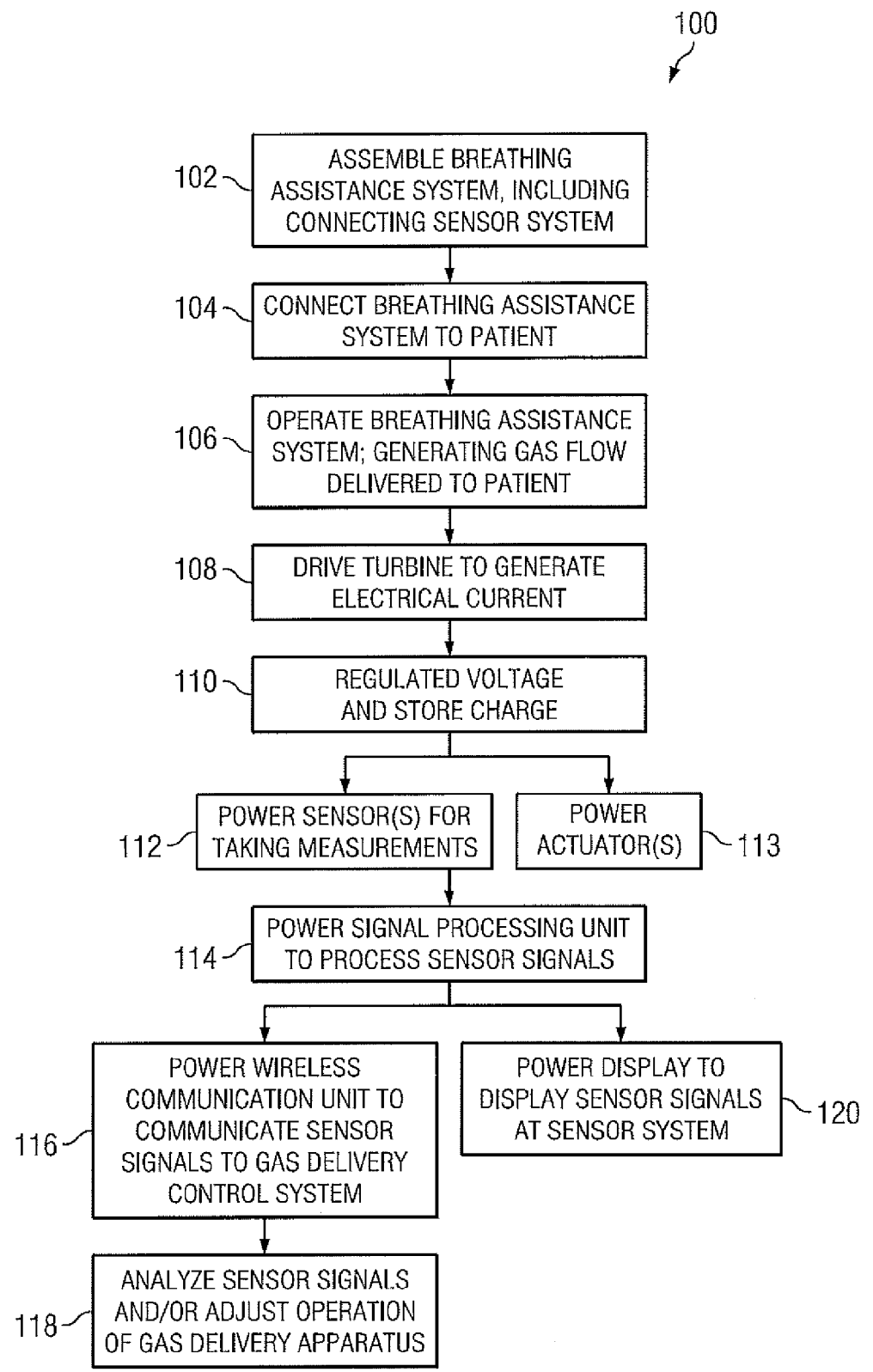
FIG. 7 is a flowchart illustrating an example method of operating a breathing assistance system including a gas flow-driven sensor system, according to certain embodiments of the present disclosure.

FIG. 7 is a flowchart illustrating an example method 100 of operating a breathing assistance system 10 including a gas flow-driven sensor system 20, according to certain embodiments of the present disclosure. At step 102, breathing assistance system 10 may be assembled, which may include connecting gas delivery system 14, connection system 18, patient interface 16, sensor system 20, and/or any other components of system 10. Sensor system 20 may be connected to one or both of connection system 18 and patient interface 16. In some embodiments, sensor system 20 may be physically integrated with one or both of connection system 18 and patient interface 16. In other embodiments sensor system 20 may be a separate component that is connected between connection system 18 and patient interface 16. Thus, sensor system 20 may include connection interfaces for connecting to certain existing models of connection systems 18 and patient interfaces 16.

At step 104, breathing assistance system 10 may be connected to a patient 12, which may include securing patient interface 16 (e.g., a tracheal tube or mask) to patient 12. At step 106, breathing assistance system 10 may be operated to provide breathing assistance to patient 12, including generating a gas flow delivered to patient 12 via connection system 18 and patient interface 16. At step 108, the gas flow drives turbine 28, causing generator 30 to generate an electrical current. At step 110, the voltage of the generated current is regulated by voltage regulator 34 and stored in charge storage device 32.

Charge storage device 32 may then supply power to any of sensor(s) 26, signal processing unit 36, wireless communication unit 38, display 40, actuator(s) 42, and/or any other electrical component of sensor system 20, as needed. For example, charge storage device 32 may supply power to one or more sensors 26 for taking one or more sensor measurements at step 112. Charge storage device 32 may then supply power to signal processing unit 36 at step 114 to process the signals from sensor(s), e.g., for display, transmission, and/or storage in memory of signal processing unit 36. Charge storage device 32 may then supply power to wireless communication unit 38 at step 116 to wirelessly communicate sensor signals to gas delivery control system 22 and/or mobile display device(s). Gas delivery control system 22 may then analyze the sensor signals, and if appropriate, adjust the operation of gas delivery apparatus 14 at step 118 (e.g., by adjusting the pressure or flow rate of the gas flow generated by gas delivery apparatus 14). Alternatively or additionally, charge storage device 32 may supply power to display 40 at step 120 to display sensor signals on display 40.

In addition to supplying power for sensor-related functions, charge storage device 32 may also supply power to one or more actuators 42 for initiating any suitable action at step 113, e.g., controlling an anti-return valve, a non-return valve, a pressure discharge valve, a gas mixture control valve, etc.

In other embodiments, system 20 may be powered by other energy sources besides (or in addition to) a turbine as discussed above. For example, system 20 may include a battery (e.g., a rechargeable or non-rechargeable battery) or solar power generator as an energy source for system 20.

Figure 8:
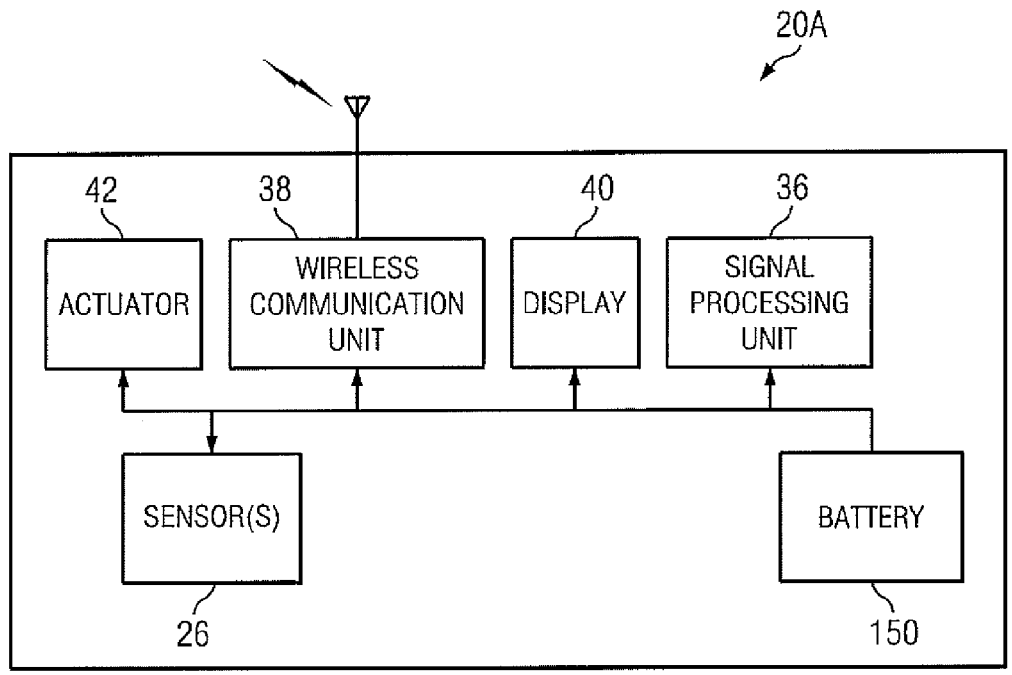
FIG. 8 illustrates an example sensor system powered by a rechargeable battery, according to certain embodiments.

FIG. 8 illustrates an example sensor system 20A powered by a rechargeable battery 150, according to certain embodiments. Battery 150 may comprise any type of rechargeable battery, e.g., one or more Lithium-ion cells. Battery 150 may supply power to any of the components of system 20, including sensor(s) 26, signal processing unit 36, wireless communication unit 38, display 40, actuator 42, and/or any other electrical component of sensor system 20, as needed, e.g., as discussed above at steps 114 and 116 of method 100 (FIG. 7).

Figure 9:
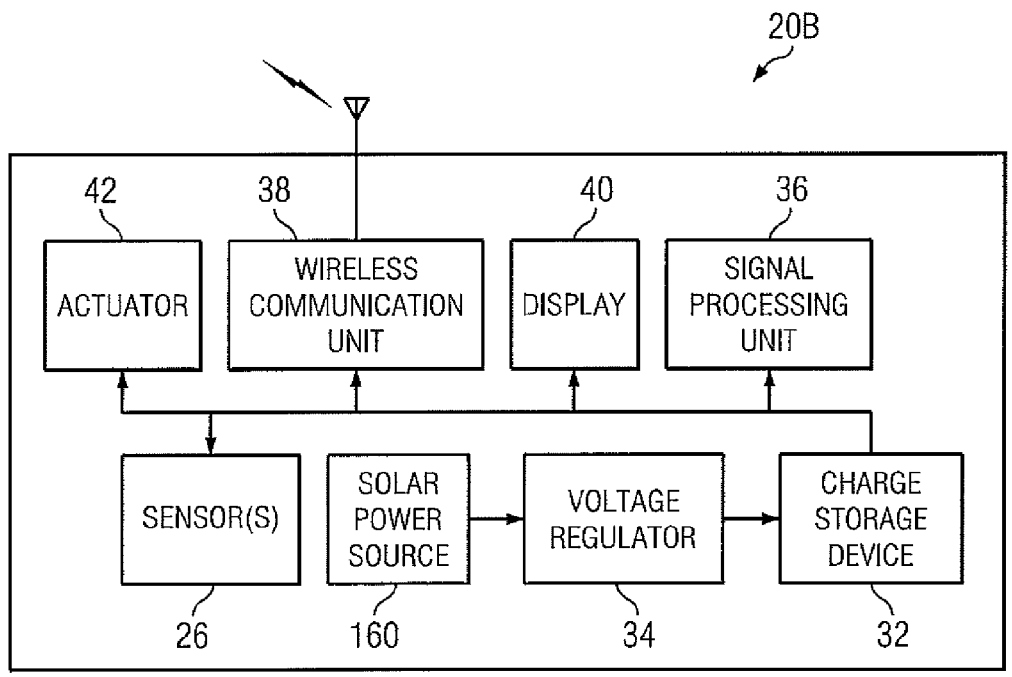
FIG. 9 illustrates an example sensor system powered by a solar power source, according to certain embodiments.

FIG. 9 illustrates an example sensor system 20B powered by a solar power source 160, according to certain embodiments. Solar power source 160 may include one or more solar cells or any other known device for converting solar or other light energy into electricity. The solar cells may be integral with or connected to one or both of patient interface 16 and connection system 18 in any suitable manner, or alternatively may be integral with or connected to a component connected between patient interface 16 and connection system 18. Solar power source 160 may provide electricity to a voltage regulator 34 for storage in a charge storage device 32, which may then may supply power to any of the components of system 20, including sensor(s) 26, signal processing unit 36, wireless communication unit 38, display 40, actuator 42, and/or any other electrical component of sensor system 20, as needed, e.g., as discussed above at steps 114 and 116 of method 100 (FIG. 7).

It will be appreciated that while the disclosure is particularly described in the context of breathing assistance systems, the apparatuses, techniques, and methods disclosed herein may be similarly applied in other contexts. For example, similar principles may be applied to any medical device that includes a gas or liquid flow suitable to drive a turbine for powering a sensor system. Additionally, it should be understood that various changes, substitutions and alterations can be made herein without departing from the spirit and scope of the disclosure as illustrated by the following claims.

What is claimed is:

1. A breathing assistance system for providing breathing assistance to a patient, comprising:
    a gas delivery system configured to generate a gas flow;
    a patient interface configured to interface with the patient;
    a connection system connected between the gas delivery system and the patient interface and configured to communicate the gas flow to the patient interface for delivery to the patient; and
    a sensor system remote from the gas delivery system and connected to at least one of the patient interface and the connection system, the sensor system including:
    a sensor for measuring a parameter of the gas flow;
    a turbine configured to be driven by the gas flow; and
    an electrical generator coupled to the turbine and configured to generate electricity for powering the sensor such that the sensor is powered by movement of the turbine;
    wherein the sensor is located upstream from the turbine such that the turbine does not significantly affect the gas flow parameter measured by the turbine-powered sensor.

2. A breathing assistance system according to claim 1, wherein the sensor system further includes an electrical charge storage device for storing electricity generated by the generator and providing electricity to the sensor, the electrical charge storage device including at least one of a battery and a capacitor.

3. A breathing assistance system according to claim 2, wherein the sensor system further includes a voltage regulator for regulating the voltage provided to the electrical charge storage device from the generator.

4. A breathing assistance system according to claim 1, wherein the sensor system further includes a signal processing unit for processing sensor signals received from the sensor for display or transmission of the sensor signals.

5. A breathing assistance system according to claim 1, wherein the sensor system further includes a wireless communication device for wirelessly transmitting sensor signals received from the sensor.

6. A breathing assistance system according to claim 5, wherein the sensor signals transmitted by the wireless communication device comprise either unprocessed sensor signals from the sensor or processed sensor signals from a processing unit coupled to the sensor.

7. A breathing assistance system according to claim 1, wherein the sensor system is powered independently of other power sources by the electricity generated by the electrical generator coupled to the turbine.

8. A breathing assistance system according to claim 1, wherein the turbine extends at least partially into the patient interface or the connection system.

9. A breathing assistance system according to claim 1, wherein the sensor system is connected in series between the patient interface and the connection system.

10. A sensor system for use in a breathing assistance system including a gas delivery system configured to generate a gas flow, a patient interface configured to interface with a patient, and a connection system connected between the gas delivery system and the patient interface and configured to communicate the gas flow to the patient interface for delivery to the patient, the sensor system comprising:
- a sensor for measuring a parameter of the gas flow;
- a turbine configured to be driven by the gas flow; and
- an electrical generator coupled to the turbine and configured to generate electricity for powering the sensor such that the sensor is powered by movement of the turbine;
- wherein the sensor system is located remote from the gas delivery system and connected to at least one of the patient interface and the connection system; and
- wherein the sensor is located upstream from the turbine such that the turbine does not significantly affect the gas flow parameter measured by the turbine-powered sensor.

11. A sensor system according to claim 10, further comprising an electrical charge storage device for storing electricity generated by the generator and providing electricity to the sensor, the electrical charge storage device including at least one of a battery and a capacitor.

12. A sensor system according to claim 11, further comprising a voltage regulator for regulating the voltage provided to the electrical charge storage device from the generator.

13. A sensor system according to claim 10, further comprising a signal processing unit for processing sensor signals received from the sensor for display or transmission of the sensor signals.

14. A sensor system according to claim 10, further comprising a wireless communication device for wirelessly transmitting sensor signals received from the sensor.

15. A sensor system according to claim 10, wherein the turbine is configured to extend at least partially into the patient interface or the connection system.

16. A sensor system according to claim 10, wherein the sensor system is configured for connection in series between the patient interface and the connection system.

17. A method for operating a sensor system in a breathing assistance system including a gas delivery system configured to generate a gas flow, a patient interface configured to interface with a patient, and a connection system connected between the gas delivery system and the patient interface and configured to communicate the gas flow to the patient interface for delivery to the patient, the method comprising:
- providing a turbine configured to be activated by the gas flow;
- generating an electrical current from the turbine activated by the gas flow; and
- powering a sensor using the electrical current generated from the turbine, the sensor configured to measure a parameter of the gas flow;
- wherein the sensor is located upstream from the turbine such that the turbine does not significantly affect the gas flow parameter measured by the turbine-powered sensor.

18. A method according to claim 17, further comprising wirelessly communicating sensor signals from the sensor to a control system associated with the gas delivery system such that the control system can adjust the gas flow generated by the gas delivery system based at least on the sensor signals.

* * * * *